United States Patent [19]

Shepherd

[11] 4,330,546

[45] May 18, 1982

[54] 3-ARYL-3-ARYLOXYPROPYLAMINES

[75] Inventor: Robin G. Shepherd, Burnham, England

[73] Assignee: John Wyeth & Brother Limited, Maidenhead, England

[21] Appl. No.: 183,786

[22] Filed: Sep. 3, 1980

[30] Foreign Application Priority Data

Sep. 14, 1979 [GB] United Kingdom ................ 7932046

[51] Int. Cl.³ .................... A61K 31/44; C07D 213/63; C07D 213/64
[52] U.S. Cl. ..................................... 424/263; 546/300
[58] Field of Search ......................... 424/263; 546/300

[56] References Cited

U.S. PATENT DOCUMENTS

| | | | |
|---|---|---|---|
| 2,683,742 | 7/1954 | Cusic | 564/346 |
| 3,106,564 | 10/1963 | Fleming et al. | 564/347 |
| 4,060,601 | 11/1977 | Baldwin | 546/300 |
| 4,194,009 | 3/1980 | Molloy et al. | 564/347 |
| 4,195,090 | 3/1980 | Frei et al. | 546/300 |

FOREIGN PATENT DOCUMENTS 2907217 8/1979 Fed. Rep. of Germany .

*Primary Examiner*—John M. Ford
*Attorney, Agent, or Firm*—George Tarnowski

[57] ABSTRACT

3-Aryl-3-aryloxyalkylamines of the general formula (I)

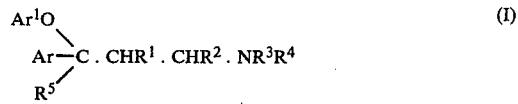

and their pharmaceutically acceptable acid addition salts, wherein $R^1$, $R^2$, $R^4$ and $R^5$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups, and $Ar^1$ is methylsulphinyl, methylsulphonyl- or cyano-substituted phenyl, 2- or 4-pyridyl, 2-pyrazinyl, 2-quinolinyl, 2-thienyl or 2-thiazolyl exhibit activity on the central nervous system, e.g. as antidepressants.

6 Claims, No Drawings

3-ARYL-3-ARYLOXYPROPYLAMINES

This invention relates to 3-aryl-3-aryloxypropylamines, to a process for preparing them, to their use and to pharmaceutical preparations containing them.

The present invention provides 3-aryl-3-aryloxypropylamines of the general formula (I)

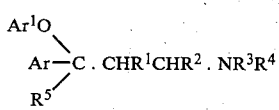

and their pharmaceutically acceptable acid addition salts, wherein $R^1$, $R^2$, $R^4$ and $R^5$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups and $Ar^1$ is methylsulphinyl-, methylsulphonyl- or cyano-substituted phenyl, 2- or 4-pyridyl, 2-pyrazinyl, 2-quinolinyl, 2-thienyl or 2-thiazolyl.

The invention also provides process for preparing a compound of general formula (I) or a pharmaceutically acceptable acid addition salt thereof, which comprises reacting an anion of an alcohol of general formula (II)

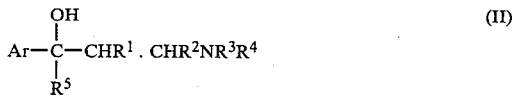

(where Ar, $R^1$, $R^2$, $R^3$, $R^4$ and $R^5$ are as defined above) with a halo compound of general formula (III)

where X is fluorine and $Ar^1$ is a methylsulphinyl-, methylsulphonyl- or cyano-substituted phenyl radical or X is fluorine, chlorine or bromine (preferably fluorine) and $Ar^1$ is 2- or 4-pyridyl, 2-pyrazinyl, 2-quinolinyl, 2-thienyl or 2-thiazolyl. The reaction may be carried out in a dipolar aprotic solvent. Examples of dipolar aprotic solvents include dimethylsulphoxide, dimethylformamide, hexamethylphosphoric triamide and sulpholane. Preferably the solvent is dimethylsulphoxide. The anion of the alcohol of general formula (II) is preferably formed by reacting the alcohol with potassium or sodium hydride or an alkyl or phenyl lithium (e.g. butyl lithium) in a compatible dipolar aprotic solvent. Preferably the alcohol is reacted with sodium hydride.

The process of the invention can be carried out at convenient temperatures e.g. 0° to 100° C. (for example room temperature); there is generally no need to use reflux temperatures. Good yields of products are generally obtained in relatively short reaction times (e.g. within two to three hours).

If in the process described above the compound of the general formula (I) is obtained as an acid addition salt, such as a pharmaceutically acceptable acid addition salt or an acid addition salt such as an oxalate, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

Once a compound of general formula (I) is obtained, if desired it can be converted into another compound of general formula (I) methods. For example, a 3-aryl-3-aryloxypropylamine of formula (I) in which both $R^3$ and $R^4$ are methyl can be converted to the compound in which one group is methyl and the other hydrogen by treatment with cyanogen bromide or ethyl or phenyl chloroformate followed by basic hydrolysis.

The compounds of general formula (I) possess one or more asymmetric carbon atoms, depending upon the particular substituents. The compounds can therefore exist in various stereochemical forms. It will be realised that if the starting material of formula (II) is a mixture of isomers the product of formula (I) will also be a mixture of isomers which may be separated, if required, by standard procedures. If the starting material is a single isomer then the product will also be a single isomer.

The term "lower" as used herein means that the radical referred to contains 1 to 6 carbon atoms. The radical preferably contains 1 to 4 carbon atoms. Examples of lower alkyl radicals include methyl, ethyl, propyl and butyl. Examples of lower alkoxy radicals include methoxy, ethoxy, propoxy and butoxy. Examples of lower alkenyl radicals include allyl and methallyl. When $R^1$, $R^2$ and/or $R^3$ represent lower alkyl, the lower alkyl group is preferably a straight chain radical such as methyl, ethyl, n-propyl or n-butyl although $R^3$ may also be, for example, a branched chain lower alkyl group such as isopropyl. $R^1$, $R^2$ and $R^5$ are preferably hydrogen.

The compounds of general formula (I) and their pharmaceutically acceptable acid addition salts, including the novel compounds of the invention, generally possess pharmacological activity. In particular the compounds exhibit activity on the central nervous system, e.g. as antidepressants, as indicated by one or more of the standard pharmacological test procedures such as the reserpine hypothermia procedure based on B. M. Askew, Life Sciences (1963), 1,725–730, the inhibition of noradrenaline or 5-hydroxytryptamine uptake in rat brain slices, the potentiation and prolongation of the effects of amphetamine and the modification of the effects of p-chloroamphetamine. For example, N-methyl-3-(2-pyridyloxy)-3-phenylpropylamine, a representative compound of the invention, in the reserpine hypothermia procedure produced a rise in rectal temperature compared to the control of 8.7° C. at 10 mg/kg and 10.7° C. at 30 mg/kg.

The invention further provides a method of treating depression which comprises administering to a warm blooded mammal animal, particularly a human, a therapeutically effective amount of a compound of the invention. The invention also provides a pharmaceutical composition comprising a compound of the invention in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form.

The following Examples illustrate the invention.

EXAMPLE 1

3-(4-Cyanophenoxy)-N,N-dimethyl-3-phenylpropylamine

A mixture of N,N-dimethyl-3-hydroxy-3-phenylpropylamine (3.58 g, 20 mM), 50% sodium hydride dispersion (1 g) and DMSO (50 ml) was heated at 80° until homogenous, cooled to ambient temperature and treated dropwise with a solution of 4-fluorobenzonitrile (2.42 g, 20 mM) in DMSO with cooling (exothermic). After 1 h the reaction mixture was poured on to water (200 ml) and extracted with ether (2×200 ml). The ether extract was extracted with 1 N hydrochloric acid (2×50 ml), the acid extract basified and then extracted with ether (2×200 ml). The ether was dried and the solvents removed under reduced pressure to give an oil which was dissolved in ethyl acetate and treated with an excess of a solution of oxalic acid dihydrate in ethyl acetate. Removal of the resultant precipitate by filtration followed by recrystallisation from ethyl acetate gave the title compound (4.8 g) as the oxalate quarter hydrate m.p. 80° (decomp). Found: C, 64.1; H, 6.05; N, 7.7% $C_{18}H_{20}N_2O.C_2H_2O_4$ requires: C, 64.1; H, 6.1; N 7.5%.

EXAMPLE 2

3-(4-Cyanophenoxy)-N-methyl-3-phenylpropylamine

A mixture of 3-hydroxy-N-methyl-3-phenylpropylamine (2.5 g, 15 mM), 50% sodium hydride dispersion (750 mg) and DMSO (50 ml) were heated at 80° until homogenous, cooled to ambient temperature and treated with a solution of 4-fluorobenzonitrile (1.82 g, 15 mM) in DMSO (10 ml). After 1 h the mixture was poured on to water (250 ml) and extracted with ether (2×250 ml). The combined ether layers were extracted with 2 N hydrochloric acid (2×25 ml), the acid extracts basified and extracted with ether (2×100 ml). The organic phase was dried, evaporated and the residue dissolved in ethyl acetate. Treatment with an excess of a solution of oxalic acid in ethyl acetate gave the title compound as the oxalate (3 g) m.p. 131°–3°.

Found: C, 64.0; H, 5.9; N, 8.0%. $C_{17}H_{18}N_2O.C_2H_2O_4$ requires: C. 64.0; H, 5.7; N, 7.9%.

EXAMPLE 3

N,N-Dimethyl-3-(2-pyridyloxy)-3-phenylpropylamine

A mixture of N,N-dimethyl-3-hydroxy-3-phenylpropylamine (4.48 g., 25 mM), prewashed 50% sodium hydride (1.25 g, 25 mM) and DMSO (50 ml) was maintained at 80° until homogenous, cooled to ambient temperature and treated with a solution of 2-fluoropyridine (2.72 g, 25 mM), in DMSO (10 ml). After 1 h the mixture was poured on to water (250 ml) and extracted with ether (2×250 ml). The combined organic extracts were washed with brine, dried and evaporated. The residue was dissolved in ethyl acetate and added to an excess of a solution of oxalic acid dihydrate in ethyl acetate. Removal of the resulting precipitate by filtration followed by drying in vacuo gave the title compound as the oxalate quarter hydrate (5.8 g) m.p. 133°–5°.

Found: C, 61.6; H,6.5; N, 7.8%. $C_{18}H_{22}N_2O_5 \cdot \frac{1}{4}H_2O$ requires: C, 61.6; H, 6.5; N, 8.0%.

EXAMPLE 4

N-Methyl-3-(2-pyridyloxy)-3-phenylpropylamine

A mixture of 3-hydroxy-N-methyl-3-phenylpropylamine (4.1 g, 25 mM), prewashed 50% sodium hydride (1.25 g, 25 mM) and DMSO (50 ml) was obtained at 80° until homogenous, cooled to ambient temperature and treated with a solution of 2-fluoropyridine (2.72 g, 25 mM) in DMSO (10 ml). After 1 h the mixture was poured on to water (250 ml) and extracted with ether (2×250 ml). The combined organic extracts were washed with brine, dried and evaporated. The residue was dissolved in ethyl acetate and added to an excess of a solution of oxalic acid in ethyl acetate. The resultant precipitate was removed by filtration and dried in vacuo to give the title compound as the oxalate (5.5 g) m.p. 161°–3° (decomp.).

Found: C, 61.1; H, 6.2; N, 8.3% $C_{15}H_{18}N_2O \cdot C_2H_2O_4$ requires: C, 61.4; H, 6.1; N, 8.4%.

EXAMPLE 5

N,N-Dimethyl-3-(4-methylsulphinylphenoxy)-3-phenylpropylamine

A mixture of N,N-dimethyl-3-hydroxy-3-phenylpropylamine (3.58 g, 20 mM), 50% sodium hydride dispersion (1 g) and DMSO (50 ml) was heated at 80° until homogenous, cooled to room temperature and treated dropwise with a solution of 1-fluoro-4-methylsulphinylbenzene (3.16 g, 20 mM) in DMSO (10 ml) (slightly exothermic). After 2 hours the reaction mixture was poured onto water (200 ml) and extracted with ether (2×200 ml). The ether layer were extracted with 1 N hydrochloric acid (2×50 ml), the extracts basified, extracted with ether (2×200 ml). The final ether extracts were dried, and the solvent removed under reduced pressure to give an oil which was taken up in ethyl acetate (250 ml) and treated with a solution of oxalic acid dihydrate (3 g) in ethyl acetate (250 ml). Removal of the resultant precipitate by filtration and drying in vacuo gave the title compound as the oxalate hemihydrate (6.3 g), m.p. 110°–112°.

Found: C, 57.75; H, 6.45; N, 3.2%. $C_{18}H_{23}NO_2S \cdot C_2H_2O_4 \cdot \frac{1}{2}H_2O$ required: C, 57.7; H, 6.3; N, 3.4%.

EXAMPLE 6

N,N-Dimethyl-3-(4-methylsulphonylphenoxy)-3-phenylpropylamine

A mixture of N,N-dimethyl-3-hydroxy-3-phenylpropylamine (3.58 g, 20 mM) 50% sodium hydride dispersion (1 g) and DMSO (50 ml) was heated at 80° until homogenous, cooled to ambient temperature and treated dropwise with a solution of 1-fluoro-4-methylsulphonylbenzene (3.48 g, 20 mM) in DMSO (10 ml) (slightly exothermic). After 1 hour the reaction mixture was poured onto water (200 ml) and extracted with ether (2×200 ml). The ether extract was extracted with 1 N hydrochloric acid (2×50 ml), the acid layer basified and extracted with ether (2×200 ml). The ether layer was dried, the solvents removed under reduced pressure, the residue dissolved in ethyl acetate and treated with an excess of a solution of oxalic acid in ethyl acetate. Removal of the resultant precipitate by filtration followed by recrystallisation from acetone gave the title compound as the oxalate (4.5 g), m.p. 182°–4°.

Found: C, 56.9; H, 6.25; N, 3.3%. $C_{18}H_{23}NO_3S \cdot C_2H_2O_4$ requires: C, 56.7; H, 6.0; N, 3.3%.

EXAMPLE 7

N,N-Dimethyl-3-phenyl-3-(2-pyrazinyloxy)propylamine

Following the method of Example 3, reaction of N,N-dimethyl-3-hydroxy-3-phenylpropylamine, sodium hydride and 2-chloropyrazine in DMSO gives the title compound.

EXAMPLE 8

N-Methyl-3-phenyl-3-(2-quinolyloxy)propylamine

Following the method of Example 4, reaction of 3-hydroxy-N-methyl-3-phenylpropylamine, sodium hydride and 2-chloroquinoline in DMSO gives the title compound.

EXAMPLE 9

N,N-Dimethyl-3-phenyl-3-(2-thiazolyloxy)propylamine

Following the method of Example 3, reaction of N,N-dimethyl-3-hydroxy-3-phenylpropylamine, sodium hydride and 2-bromothiazole in DMSO gives the title compound.

EXAMPLE 10

N-Methyl-3-phenyl-3-(2-thienyloxy)propylamine

Following the method of Example 4, reaction of 3-hydroxy-N-methyl-3-phenylpropylamine, sodium hydride and 2-fluorothiophen in DMSO gives the title compound.

EXAMPLE 11

N,N-Dimethyl-3-(4-pyridyloxy)-3-phenylpropylamine

A solution of the sodium salt of N,N-dimethyl-3-hydroxy-3-phenylpropylamine in DMSO is generated as in Example 3 then treated with a solution of 4-chloropyridine in ether (generated by dissolving 4-chloropyridine hydrochloride in water, adjusting the pH to 8.5 with sodium bicarbonate, extracting the aqueous solution with toluene, evaporating the toluene under reduced pressure and dissolving the residue in ether).

Aqueous work up of the reaction mixture as in Example 3 gives the title compound.

I claim:

1. A compound selected from the group consisting of a 3-aryl-3-aryloxypropylamine of the formula

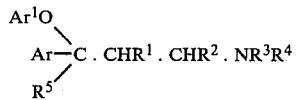

and a pharmaceutically acceptable acid addition salt thereof wherein $R^1$, $R^2$, $R^4$ and $R^5$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups, and $Ar^1$ is 2- or 4-pyridyl.

2. A compound as claimed in claim 1 wherein $R^1$, $R^2$ and $R^5$ are all hydrogen.

3. A compound as claimed in claim 1 which is N,N-dimethyl-3-(2-pyridyloxy)-3-phenylpropylamine or a pharmaceutically acceptable acid addition salt thereof.

4. A compound as claimed in claim 1 which is N-methyl-3-(2-pyridyloxy)-3-phenylpropylamine or a pharmaceutically acceptable acid addition salt thereof.

5. A pharmaceutical composition having antidepressant activity which comprises a compound selected from the group consisting of a 3-aryl-3-aryloxypropylamine of the formula

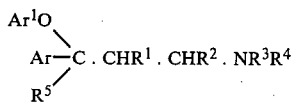

and a pharmaceutically acceptable acid addition salt thereof wherein $R^1$, $R^2$, $R^4$ and $R^5$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups, and Ar$^1$ is 2- or 4-pyridyl in association with a pharmaceutically acceptable carrier.

6. A method of treating depression in a warm blooded mammal which comprises administering to said mammal an antidepressantly effective amount of a compound selected from the group consisting of a 3-aryl-3-aryloxypropylamine of the formula

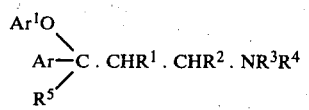

and a pharmaceutically acceptable acid addition salt thereof, wherein $R^1$, $R^2$, $R^4$ and $R^5$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups and Ar$^1$ is 2- or 4-pyridyl.

* * * * *